US012766043B2

(12) United States Patent
Fitzpatrick

(10) Patent No.: US 12,766,043 B2
(45) Date of Patent: Oct. 20, 2026

(54) COMPRESSION CLOTHING DEVICES

(71) Applicant: Teresa Fitzpatrick, Battle Creek, MI (US)

(72) Inventor: Teresa Fitzpatrick, Battle Creek, MI (US)

( * ) Notice: Subject to any disclaimer, the term of this patent is extended or adjusted under 35 U.S.C. 154(b) by 270 days.

(21) Appl. No.: 18/537,460

(22) Filed: Dec. 12, 2023

(65) Prior Publication Data

US 2025/0186264 A1 Jun. 12, 2025

(51) Int. Cl.
*A61F 13/08* (2006.01)

(52) U.S. Cl.
CPC .................................... *A61F 13/08* (2013.01)

(58) Field of Classification Search
CPC ........................................................ A61F 13/08
USPC ................................................................ 2/69
See application file for complete search history.

(56) References Cited

U.S. PATENT DOCUMENTS

| | | | | |
|---|---|---|---|---|
| 7,950,071 | B2 | 5/2011 | Jeong | |
| 9,610,199 | B2 | 4/2017 | Sesi | |
| D896,498 | S * | 9/2020 | Lin | D2/994 |
| 11,134,725 | B2 | 10/2021 | Erkus | |
| D955,735 | S | 6/2022 | Li | |
| D1,015,725 | S * | 2/2024 | Jesch | D2/980 |
| 2008/0249454 | A1 | 10/2008 | Mills | |
| 2015/0107000 | A1 | 4/2015 | Tanaka | |
| 2015/0230552 | A1 | 8/2015 | Metcalf | |
| 2017/0071264 | A1 * | 3/2017 | Towfigh | A41C 1/10 |
| 2017/0258641 | A1 | 9/2017 | Stein | |
| 2017/0354543 | A1 * | 12/2017 | Mazourik | A61H 1/008 |
| 2019/0254852 | A1 * | 8/2019 | Ryndziewicz | A61F 5/0104 |
| 2022/0047004 | A1 | 2/2022 | Betts | |
| 2022/0125646 | A1 | 4/2022 | Hsiao | |
| 2022/0241100 | A1 | 8/2022 | Eom | |

FOREIGN PATENT DOCUMENTS

WO WO2011025396 3/2011

* cited by examiner

*Primary Examiner* — Alissa J Tompkins
*Assistant Examiner* — Catherine M Ferreira

(57) ABSTRACT

A compression clothing devices for promoting blood circulation includes a garment being comprised of a blended fiber material. The blended fiber material may include cotton and spandex. A plurality of stripes is positioned on the garment. Each of the plurality of stripes comprises a nylon material so that each of the plurality of stripes applies pressure to a body of a user and facilitates a circulation of blood of a user.

5 Claims, 6 Drawing Sheets

COMPRESSION CLOTHING DEVICES

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to compression garments and more particularly pertains to a new compression garment for promoting blood circulation.

(2) Description of Related Art Including Information Disclosed Under 37 CFR 1.97 and 1.98

The prior art relates to compression garments. The prior art discloses compression stockings made from nylon or spandex which apply pressure to the foot and leg of a user, for example to treat and prevent foot and ankle injuries. Some of these compression stockings have design indicia printed on them, such as colorful stripes or patterns, to enhance the aesthetic appeal of the stockings. However, there is a need in the art for compression stockings that can facilitate a directed circulation of blood to and from the foot of the user. Such stockings would be highly useful for preventing the foot of the user from losing circulation and for preventing the blood from pooling in the foot of the user. There is also a need in the art for other compressive garments that can promote blood circulation and inhibit fatigue for the legs, back, and torso of the user.

BRIEF SUMMARY OF THE INVENTION

An embodiment of the disclosure meets the needs presented above by generally comprising a garment that comprises a blended fiber material. The blended fiber material may include cotton and spandex. A plurality of stripes is positioned on the garment.

Each of the plurality of stripes comprises a nylon material whereby the plurality of stripes is configured to apply pressure to a body of a user thereby facilitating a circulation of blood of a user.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
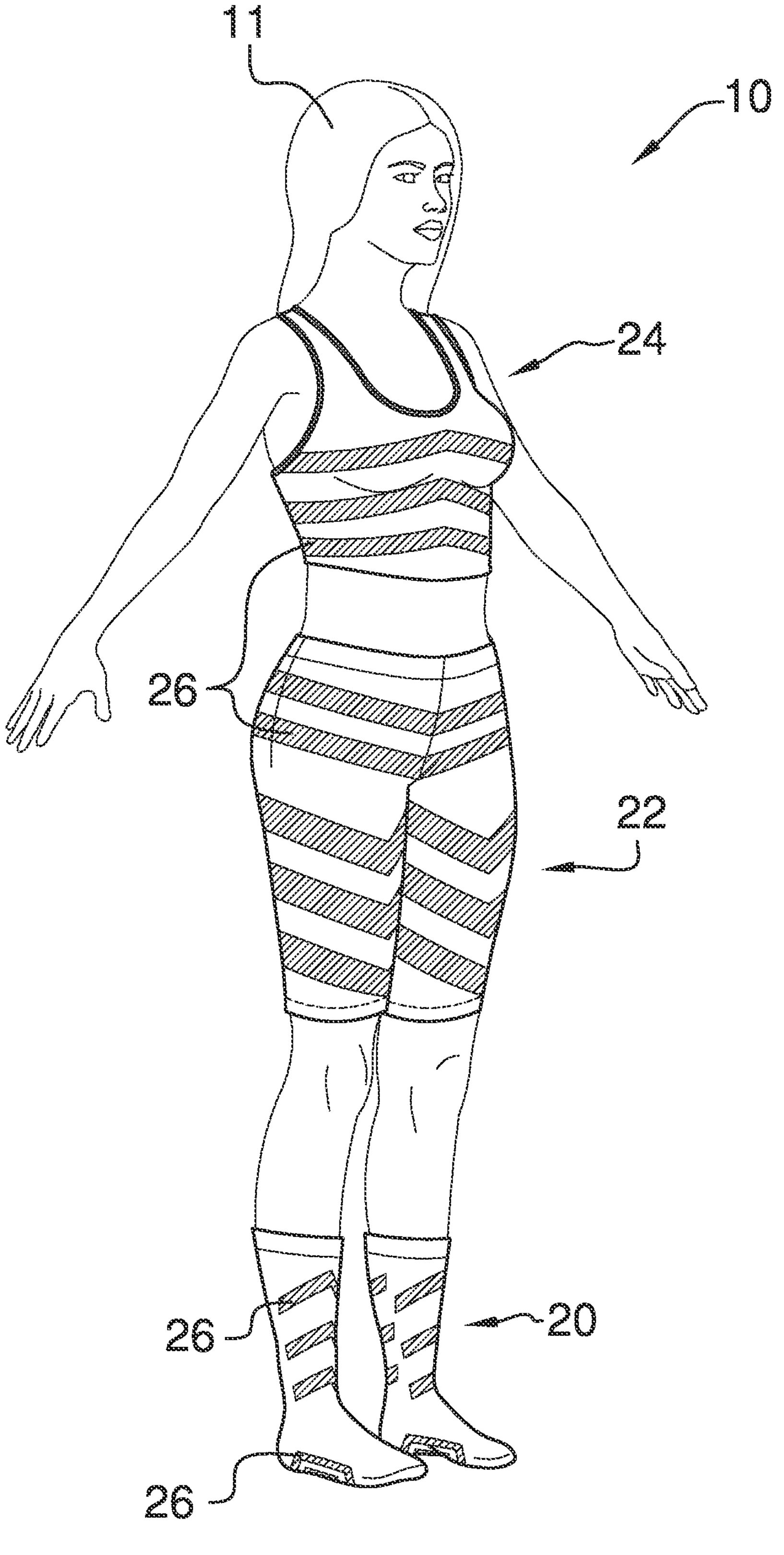
FIG. 1 is an isometric in-use view of a compression clothing devices according to an embodiment of the disclosure.
Figure 2:
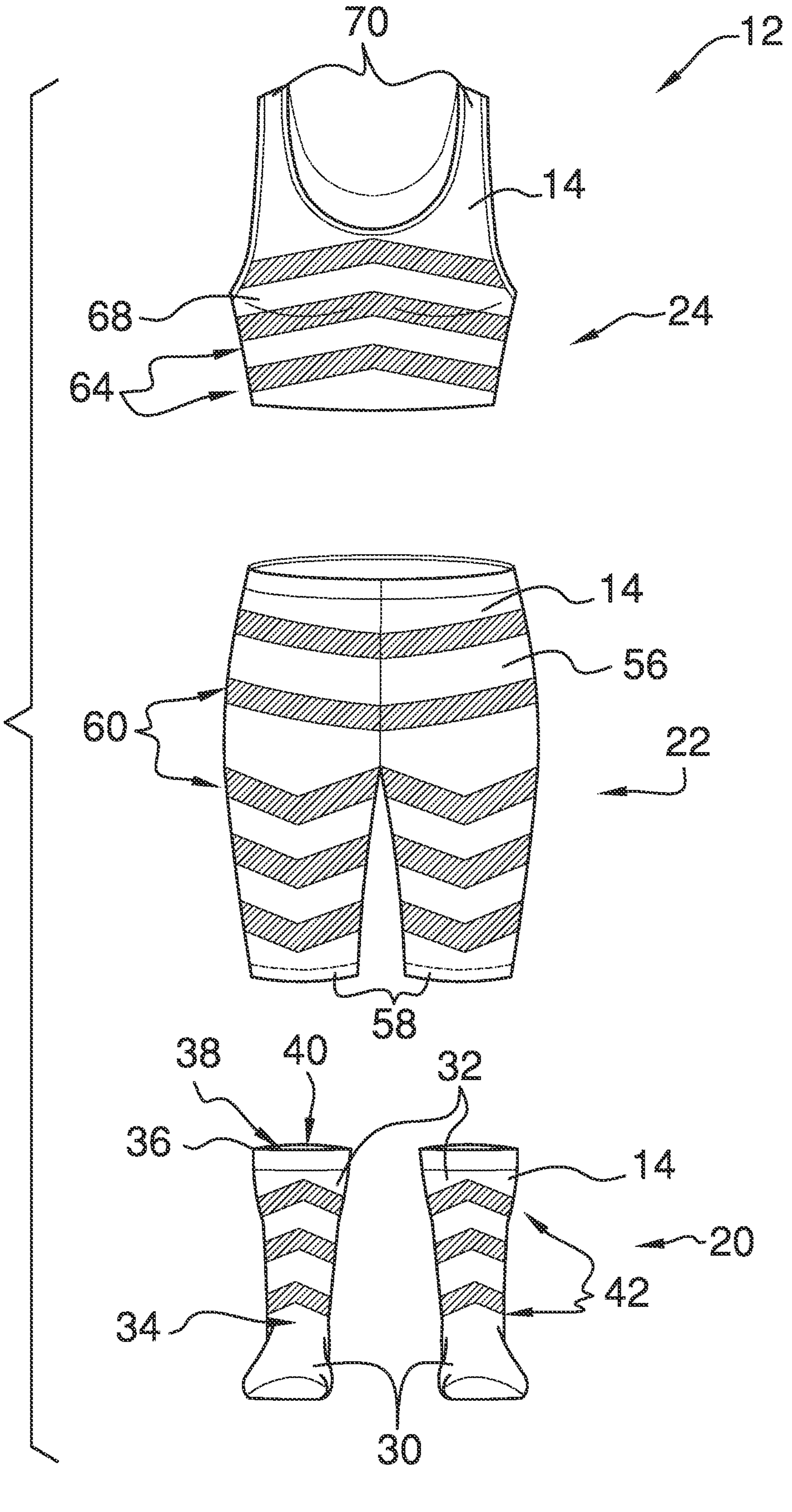
FIG. 2 is a front view of an embodiment of the disclosure.

With reference now to the drawings, and in particular to FIGS. 1 through 7 thereof, a new compression garment embodying the principles and concepts of an embodiment of the disclosure and generally designated by the reference numeral 10 will be described.

As best illustrated in FIGS. 1 through 7, the compression clothing device 10 generally comprises a garment 12 having a front side 14 and a back side 16. The garment 12 is generally comprised of a blended fiber material 18. The blended fiber material 18 may include cotton and spandex. As used in this description, the blended fiber material 18 is a mixture of two or more textile fibers, which typically include cotton and spandex fibers blended together. In some examples, this blend of cotton and spandex fibers can improve the stretching properties and inhibit odors in the garment 12. The garment 12 may be a sock 20, a pant 22, or a shirt 24.

A plurality of stripes 26 is positioned on the garment 12. Each of the plurality of stripes 26 comprises a nylon material 28 whereby the plurality of stripes 26 are configured to facilitate a circulation of blood of a user 11. Each of the plurality of stripes 26 is generally spaced from the others wherein the blended fiber material 18 is positioned between each of the plurality of stripes 26. In some embodiments, each of the plurality of stripes 26 has a width between 0.5 inch and 1.5 inch.

As used in this description, a stripe is a long narrow band or strip, typically of the same width throughout its length, differing in texture or material from the surface on either side of it. In other words, a stripe is not merely an indicia or decoration positioned on the garment 12, but rather a band or strip of material that differs from the blended fiber material 18 surrounding each of the plurality of stripes 26 on the garment 12.

In some embodiments, the sock 20 further comprises a foot portion 30 that is coupled to a leg portion 32. The sock 20, or each of the foot portion 30 and the leg portion 32, has an exterior surface 34. The leg portion 32 extends upwardly from the foot portion 30 to a top edge 36 defining an opening 38 extending inwardly into the exterior surface 34. In other words, the opening 38 provides access to an interior pocket 40 of the sock 20. The interior pocket 40 is generally configured to receive a foot and a leg of the user 11.

In such embodiments, the plurality of stripes 26 further comprises a front sock set 42 that is positioned on the front side 14 of the leg portion 32. Each stripe of the front sock set 42 of the plurality of stripes 26 is aligned with the others over the front side 14 of the sock 20. Each stripe of the front sock set 42 of the plurality of strips 26 comprises an upwardly pointed arrow whereby the front sock set 42 of the plurality of stripes 26 is configured to facilitate the circulation of blood of the user 11 upwardly from the foot of the user 11 when the user 11 is wearing the sock 20.

The plurality of stripes 26 may further comprise a back sock set 44 of the plurality of stripes 26 that is positioned on the back side 16 of the leg portion 32. Each stripe of the back sock set 44 of the plurality of stripes 26 is aligned with the others over the back side 16 of the sock 20. Each stripe of the back sock set 44 of the plurality of stripes 26 comprises a downwardly pointed arrow whereby the back sock set 44 of the plurality of stripes 26 is configured to facilitate the circulation of blood of the user 11 downwardly toward the foot of the user 11 when the user 11 is wearing the sock 20.

The front sock set 42 and the back sock set 44 may be spaced from each other, wherein the blended fiber material 18 is between the opposing lateral ends of each stripe of the front sock set 42 and the back sock set 44 whereby each stripe of the front sock set 42 and the back sock set 44 is surrounded by the blended fiber material 18. An example of this embodiment is provided in FIGS. 1 and 3.

The front sock set 42 of the plurality of stripes 26 is configured to apply a directed pressure to the leg of the user 11 corresponding to a shape of the upwardly pointed arrow of each stripe of the front sock set 42. The front sock set 42 of the plurality of stripes 26 is thereby configured to facilitate an upwardly directed circulation of blood of the user 11 and inhibit the blood of the user from collecting in the foot of the user. The back sock set 44 of the plurality of stripes 26 is configured to apply a directed pressure to the leg of the user corresponding to a shape of the downwardly pointed arrow of each stripe of the back sock set 44. The back sock set 44 of the plurality of stripes 26 is thereby configured to facilitate a downwardly directed circulation of blood of the user 11 through the leg of the user 11 and toward the foot of the user 11 to inhibit the foot of the user 11 from losing the circulation.

The plurality of stripes 26 on the sock 20 may further comprise a foot set 46 of the plurality of stripes 26 that is positioned on the back side 16 of the foot portion 30. Each stripe of the foot set 46 of the plurality of stripes 26 comprises a bucket shape having a pair of side portions 48 extending outwardly from opposing lateral ends of a middle portion 50. The foot set 46 of the plurality of stripes 26 may include a first pair of stripes 52 and a second pair of stripes 54. Each stripe of the first pair of stripes 52 is spaced from the other. Each stripe of the second pair of stripes 54 is spaced from the other. The first pair of stripes 52 is spaced from the second pair of stripes 54. The second pair of stripes 54 may be positioned within the first pair of stripes 52. Each stripe of the second pair of stripes 54 may be positioned within the bucket shape between the pair of side portions 48 of a respective one of the first pair of stripes 52. The middle portion 50 of each of the second pair of stripes 54 is accordingly aligned with the middle portion 50 of the respective one of the first pair of stripes 52 such that each of the first pair of stripes 52 and the second pair of stripes 54 forms a hexagon shape. The foot set 46 of the plurality of stripes 26 is thereby configured to facilitate the circulation of blood of the user 11 around a sole of the foot of the user 11 when the user 11 is wearing the sock 20.

The blended fiber material 18 is generally positioned between each stripe of the first pair of stripes 52 and each one of the second pair of stripes 54. The blended fiber material 18 is also generally positioned between the first pair of stripes 52 and second pairs of stripes 54 such that none of the stripes of the foot set 46 of the plurality of stripes 26 are touching or contacting any of the others. In other words, each stripe of the foot set 46 of the plurality of stripes 26 is surrounded by the blended fiber material 18.

Figure 7:
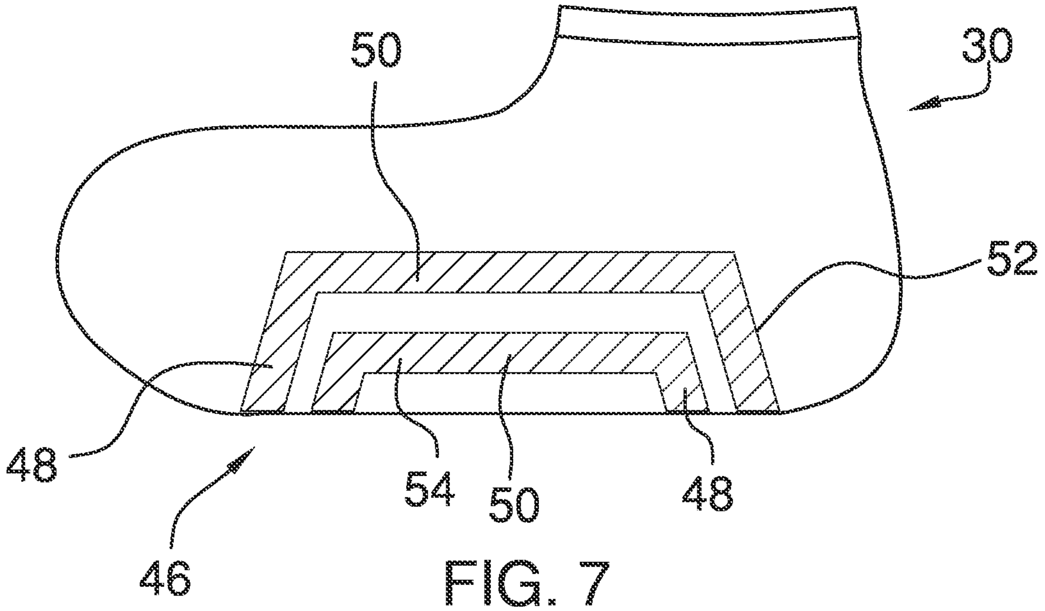
FIG. 7 is a side view of an embodiment of the disclosure.

In some embodiments, the sock 30 comprises the foot portion 30, but not the leg portion 32, as shown in FIG. 7. The plurality of stripes 26 in such embodiments includes the foot set 46 that facilitates the circulation of blood around the sole of the foot of the user 11, as described above and depicted in FIGS. 5 and 7.

The pant 22 may further comprise a waist portion 56 that is coupled to a pair of leg portions 58. Each of the pair of leg portions 58 extends downwardly from the waist portion 56. The plurality of stripes 26 on the pant 22 includes a front pant set 60 and a back pant set 62.

The front pant set 60 of the plurality of stripes 26 is positioned on the front side 14 of the pant 22. Each stripe of the front pant set 60 of the plurality of stripes 26 on the waist portion 56 is concavely arcuate between opposing lateral sides of the pant 22. Each stripe of the front pant set 60 of the plurality of stripes 26 on each of the pair of leg portions 58 comprises a downwardly pointed arrow. The the front pant set 60 of the plurality of stripes 26 is thus configured to facilitate the circulation of blood downwardly from a waist of the user 11 when the user 11 is wearing the pant.

The back pant set 62 of the plurality of stripes 26 is positioned on the back side 16 of the pant 22. Each stripe of the back pant set 62 of the plurality of stripes 26 may comprise an upwardly pointed arrow whereby the back pant set 62 of the plurality of stripes 26 is configured to facilitate the circulation of blood upwardly toward a waist of the user 11 when the user 11 is wearing the pant 22.

Figure 3:
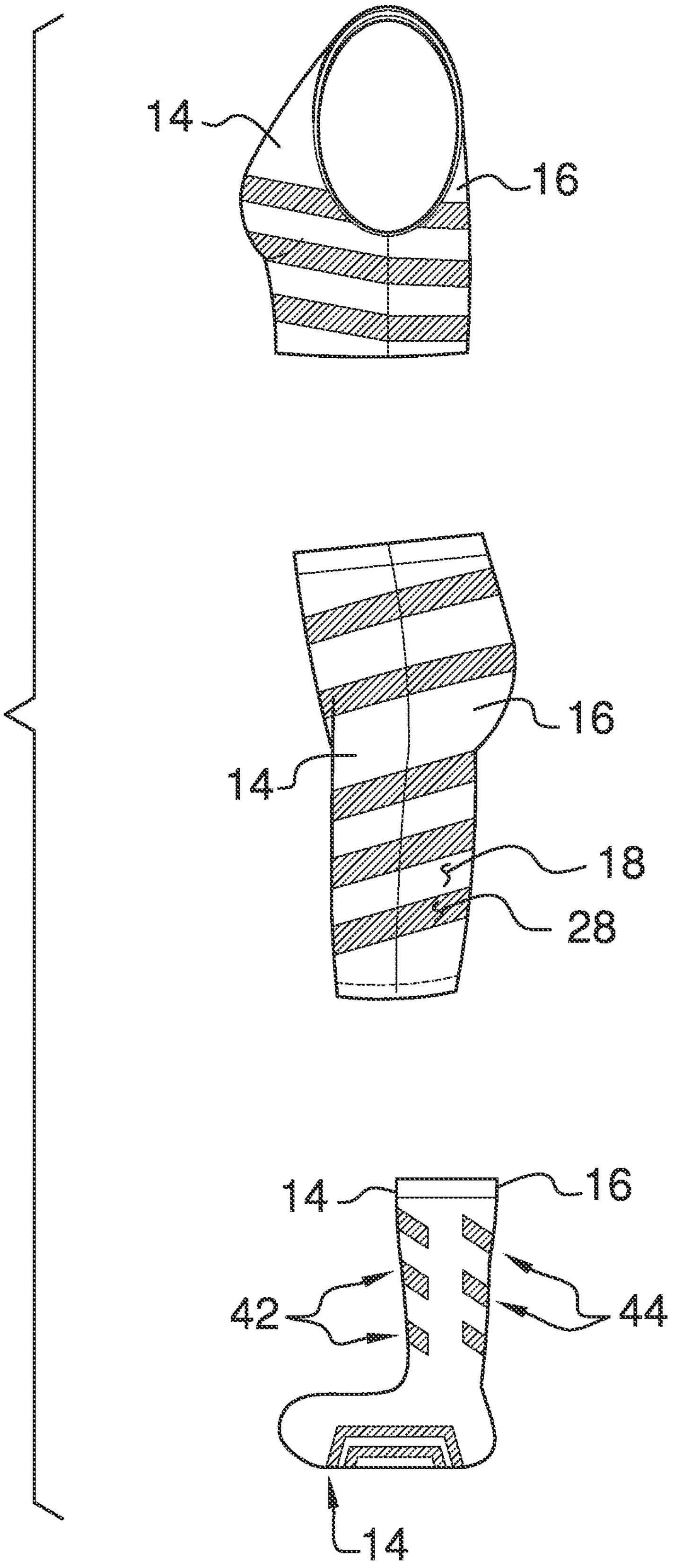
FIG. 3 is a side view of an embodiment of the disclosure.

As shown in FIGS. 1 and 3, opposing lateral ends of the front pant set 60 of the plurality of stripes 26 may be in contact with opposing lateral ends of the back pant set 62 of the plurality of stripes 26 such that the front pant set 60 and the back pant set 62 form continuous bands of the nylon material 28 between the front side 14 of the pant 22 and the back side 16 of the pant 22.

The shirt 24 may further comprise a torso portion 68 coupled to a pair of arm portions 70. The plurality of stripes 26 may be positioned on the torso portion 68 of the shirt 24. The plurality of stripes 26 may include a front shirt set 64 and a back shirt set 66.

The front shirt set 64 of the plurality of stripes 26 is positioned on the front side 14 of the shirt 24. Each stripe of the front shirt set 64 of the plurality of stripes 26 may comprise an upwardly pointed arrow whereby the front shirt set 64 of the plurality of stripes 26 is configured to facilitate the circulation of blood upwardly toward a head of the user 11 when the user 11 is wearing the shirt.

Figure 4:
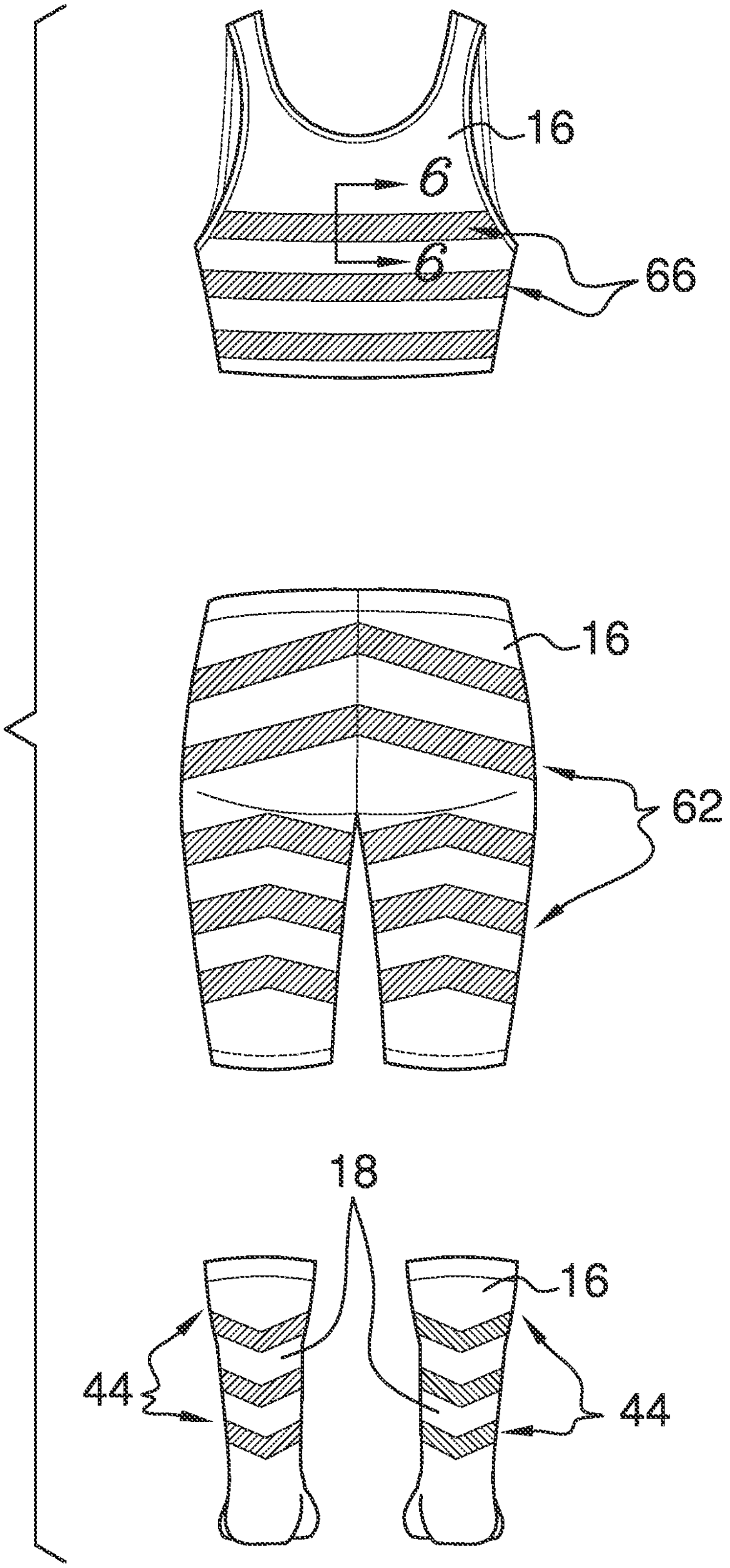
FIG. 4 is a back view of an embodiment of the disclosure.
Figure 5:
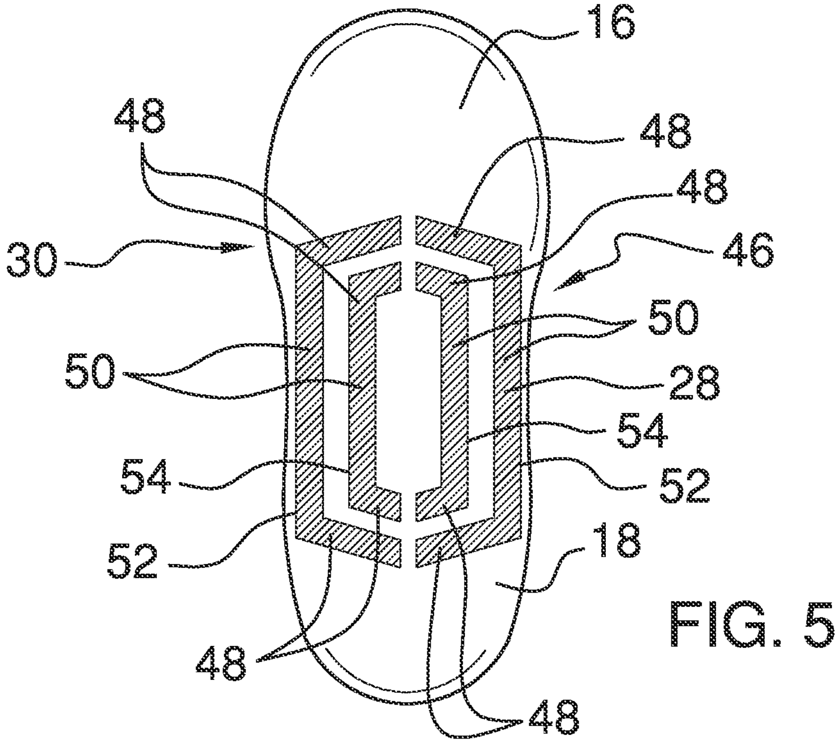
FIG. 5 is a bottom view of an embodiment of the disclosure.
Figure 6:
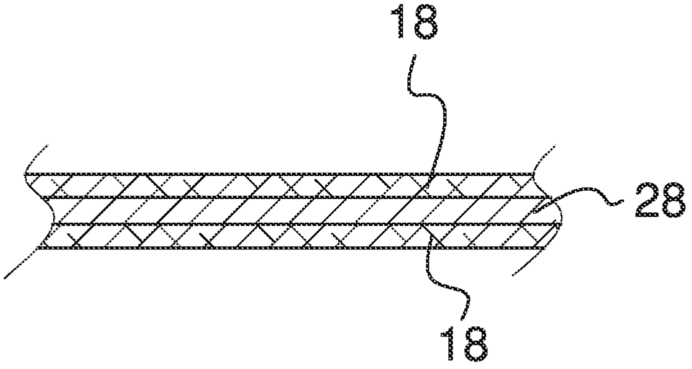
FIG. 6 is a cross-sectional view of an embodiment of the disclosure.

The back shirt set 66 of the plurality of stripes 26 is positioned on the back side 16 of the shirt 24. Each stripe of the back shirt set 66 of the plurality of stripes 26 is generally a straight band that is parallel with the others, as shown in FIG. 4. The the back shirt set 66 of the plurality of stripes 26 is configured to facilitate the circulation of blood around a back of the user 11 when the user 11 is wearing the shirt 24.

Similar to the pant 22, opposing lateral ends of the front shirt set 64 of the plurality of stripes 26 may be in contact with opposing lateral ends of the back shirt set 66 of the plurality of stripes 26 such that the front shirt set 64 and the back shirt set 66 form continuous bands of the nylon material between the front side 14 of the shirt 24 and the back side 16 of the shirt 24.

Generally, each stripe of the various sets of stripes on each particular garment 12 will be parallel with the other stripes in that set. For example, each stripe in the front sock set 42 is parallel with the other stripes in the front sock set 42 and each stripe in the back sock set 44 is parallel with the other stripes in the back sock set 44. The pair of side portions 48 of the first pair of stripes 52 on the back side 16 of the foot portion 30 are generally parallel with the pair of side portions 48 of the second pair of stripes 54 on the back side 16 of the foot portion 30.

In use, the user 11 can wear one or more of the garments 12 to facilitate the circulation of blood throughout the body of the user 11. For example, the user 11 can wear the sock 20 to facilitate the circulation of blood through the calf, shin, and foot of the user 11. In another example, the user 11 can wear the embodiment of the sock 20 shown in FIG. 7 to facilitate the circulation of blood through the foot of the user 11. The user 11 may wear the pant 22 to facilitate the circulation of blood through the legs of the user 11, or the shirt 24 to facilitate the circulation of blood through the torso of the user 11. While the user 11 is wearing the garment, nylon material 28 of the plurality of stripes 26 will apply a pressure to the area of the body corresponding to the position of each stripe of the plurality of stripes 26. The nylon material 28 may compress the muscles to help blood flow through the body more efficiently or to prevent blood from pooling in the body. The pressure applied by the nylon material 28 will facilitate the application of the pressure in a particular direction to facilitate the circulation of blood in those directions. For example, the upwardly and downwardly pointed arrows of the front sock set 42 and the back sock set 44 facilitate the circulation of blood upwardly and downwardly along the front and back of the leg of the user 11, respectively.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A compression garment assembly comprising:

a garment being comprised of a blended fiber material, the blended fiber material including cotton and spandex, the garment being a sock having a front side, a back side, a foot portion, and a leg portion; and a plurality of stripes being positioned on the garment, each of the plurality of stripes comprising a nylon material whereby the plurality of stripes is configured to apply pressure to a body of a user thereby facilitating a circulation of blood of a user, the plurality of stripes including:

a front sock set of the plurality of stripes being positioned on the front side of the leg portion;

a back sock set of the plurality of stripes being positioned on the back side of the leg portion; and a foot set of the plurality of stripes being positioned on the back side of the foot portion wherein the foot set of the plurality of stripes are spaced from the front sock set and the back sock set and wherein the foot set of the plurality of stripes are configured for being positioned on a sole of a foot to facilitate the circulation of blood around the sole of the foot, each of the foot set of the plurality of stripes comprising a bucket shape having a pair of side portions extending outwardly from opposing lateral ends of a middle portion, the foot set of the plurality of stripes including a first pair of stripes and a second pair of stripes, each of the first pair of stripes being spaced from the other, each of the second pair of stripes being spaced from the other, the second pair of stripes being positioned within the first pair of stripes whereby each of the second pair of stripes is positioned within the bucket shape between the pair of side portions of a respective one of the first pair of stripes and whereby the middle portion of each of the second pair of stripes is aligned with the middle portion of the respective one of the first pair of stripes such that the foot set of the plurality of stripes forms a hexagon shape, the foot set of the plurality of stripes thereby being configured to direct the circulation of blood of the user around the sole of the foot of the user when the user is wearing the sock.

2. The compression garment assembly of claim 1, wherein each of the plurality of stripes is spaced from the others whereby the blended fiber material is positioned between the plurality of stripes.

3. The compression garment assembly of claim 1, the sock further comprising:

the leg portion extending upwardly from the foot portion to a top edge defining an opening extending inwardly into an interior pocket of the sock, the interior pocket being configured to receive a foot and a leg of the user wherein the front sock set of the plurality of stripes are aligned with each other over the front side of the sock, each of the front sock set of the plurality of stripes comprising an upwardly pointed arrow whereby the front sock set of the plurality of stripes is configured to facilitate the circulation of blood of the user upwardly from the foot of the user when the user is wearing the sock and wherein the back sock set of the plurality of stripes are aligned with each other over the back side of the sock, each of the back sock set of the plurality of stripes comprising a downwardly pointed arrow whereby the back sock set of the plurality of stripes is configured to facilitate the circulation of blood of the user downwardly toward the foot of the user when the user is wearing the sock.

4. A compression garment assembly comprising:

a garment having a front side and a back side, the garment being comprised of a blended fiber material, the blended fiber material including cotton and spandex, the garment being a sock having a front side, a back side, a foot portion, and a leg portion; and a plurality of stripes being positioned on the garment, each of the plurality of stripes comprising a nylon material whereby the plurality of stripes is configured to apply pressure to a body of a user thereby facilitating a circulation of blood of a user, each of the plurality of stripes being spaced from the others wherein the blended fiber material is positioned between each of the plurality of stripes, the plurality of stripes including:

a front sock set of the plurality of stripes being positioned on the front side of the leg portion;

a back sock set of the plurality of stripes being positioned on the back side of the leg portion; and a foot set of the plurality of stripes being positioned on the back side of the foot portion wherein the foot set of the plurality of stripes are spaced from the front sock set and the back sock set and wherein the foot set of the plurality of stripes are configured for being positioned on a sole of a foot to facilitate the circulation of blood around the sole of the foot, each of the foot set of the plurality of stripes comprising a bucket shape having a pair of side portions extending outwardly from opposing lateral ends of a middle portion, the foot set of the plurality of stripes including a first pair of stripes and a second pair of stripes, each of the first pair of stripes being spaced from the other, each of the second pair of stripes being spaced from the other, the second pair of stripes being positioned within the first pair of stripes whereby each of the second pair of stripes is positioned within the bucket shape between the pair of side portions of a respective one of the first pair of stripes and whereby the middle portion of each of the second pair of stripes is aligned with the middle portion of the respective one of the first pair of stripes such that the foot set of the plurality of stripes forms a hexagon shape, the foot set of the plurality of stripes thereby being configured to direct the circulation of blood of the user around the sole of the foot of the user when the user is wearing the sock.

5. The compression garment assembly of claim 4, wherein each of the foot portion and the leg portion have an exterior surface, the leg portion extending upwardly from the foot portion to a top edge defining an opening extending inwardly into the exterior surface, the opening providing access to an interior pocket of the sock, the interior pocket being configured to receive the foot and a leg of the user, the front sock set of the plurality of stripes being aligned with each other over the front side of the sock, each of the front sock set of the plurality of stripes comprising an upwardly pointed arrow whereby the front sock set of the plurality of stripes is configured to facilitate the circulation of blood of the user upwardly from the foot of the user when the user is wearing the sock, the back sock set of the plurality of stripes being aligned with each other over the back side of the sock, each of the back sock set of the plurality of stripes comprising a downwardly pointed arrow whereby the back sock set of the plurality of stripes is configured to facilitate the circulation of blood of the user downwardly toward the foot of the user when the user is wearing the sock the front sock set and the back sock set being spaced from each other, the blended fiber material being between the front sock set and the back sock set, and wherein the blended fiber material is between each of the first pair of stripes and each of the second pair of stripes.

* * * * *